United States Patent
Langley et al.

(10) Patent No.: US 6,994,692 B2
(45) Date of Patent: Feb. 7, 2006

(54) INJECTION DEVICE

(75) Inventors: Christopher Nigel Langley, Leamington Spa (GB); Robert Woolston, Moreton Morrell (GB)

(73) Assignee: DCA Design International Limited, Warwick (GB)

( * ) Notice: Subject to any disclaimer, the term of this patent is extended or adjusted under 35 U.S.C. 154(b) by 0 days.

(21) Appl. No.: 10/471,730

(22) PCT Filed: Mar. 26, 2002

(86) PCT No.: PCT/GB02/01446

§ 371 (c)(1),
(2), (4) Date: Sep. 15, 2003

(87) PCT Pub. No.: WO02/076538

PCT Pub. Date: Oct. 3, 2002

(65) Prior Publication Data

US 2004/0092877 A1  May 13, 2004

(30) Foreign Application Priority Data

Mar. 27, 2001 (GB) .................................. 0107609

(51) Int. Cl.
*A61M 1/00* (2006.01)

(52) U.S. Cl. ...................................... 604/151; 604/246

(58) Field of Classification Search ................ 604/131, 604/135, 151, 246, 152, 154, 155

See application file for complete search history.

(56) References Cited

U.S. PATENT DOCUMENTS

| 4,381,006 | A | | 4/1983 | Genese |
|---|---|---|---|---|
| 5,261,882 | A | | 11/1993 | Sealfon |
| 5,637,095 | A | * | 6/1997 | Nason et al. ............... 604/135 |
| 6,110,149 | A | | 8/2000 | Klitgaard et al. |

FOREIGN PATENT DOCUMENTS

| DE | 33 31 424 A1 | 3/1984 |
|---|---|---|
| EP | 0 462 508 A1 | 12/1991 |
| EP | 0 567 923B A1 | 11/1993 |
| WO | WO 98/57688 | 12/1998 |

* cited by examiner

Primary Examiner—Kevin C. Simmons
(74) Attorney, Agent, or Firm—Oliff & Berridge, PLC

(57) ABSTRACT

Injection devices are known for the self administration of a medicament by patients. The medicament is typically contained within a cartridge located within an injection device. It is a problem that injection devices should be small enough to fit into a jacket pocket or a hand bag without difficulty. Concurrently, the injection device must be of a size that enables a piston used to drive a cartridge bung within the cartridge to both to a maximum dispense position within the cartridge and to be fully withdrawn from the cartridge to allow for replacement of the cartridge. A drive mechanism for an injection device is disclosed comprising a piston member (10), a semi rigid belt (12) connected at a first end to the piston member (10), a belt drive means to drive the semi rigid belt (12) and a dose setting mechanism to control the driving of the semi rigid belt (12) in which the belt drive means comprises a first cable means (22) connected at a first end to a second end of the semi rigid belt (12) and at a second end to a first spool (24). An injection device comprising such a drive mechanism is also disclosed.

8 Claims, 2 Drawing Sheets

INJECTION DEVICE

The present invention relates to improvements in an injection device, and in particular to improvements in a portable injection device for dispensing controlled quantities of a medicament.

Injection devices are known for the self administration of a medicament by patients. For example, those suffering from diabetes may require regular injections of insulin, others may require regular injections of a growth hormone. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This is a particular problem for the elderly, the infirm, those suffering from vision difficulties and those suffering from diabetes related problems which impair their faculties.

The medicament is typically contained within a cartridge located within the injection device. The cartridge has a bung or piston at one end which is driven towards a second end of the cartridge to expel the medicament from the injection device. It is a problem that injection devices should be small enough to fit into a jacket pocket or a hand bag without difficulty. At the same time, the injection device must be of a size that enables a piston or the like used to drive the cartridge bung within the cartridge to be moved both to a maximum dispense position within the cartridge and to be fully withdrawn from the cartridge to allow for replacement of the cartridge.

It is an advantage of the present invention that it provides a solution to these conflicting requirements.

According to a first aspect of the present invention, a drive mechanism for an injection device in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge, in which the drive mechanism comprises a piston member, a semi rigid belt connected at a first end to the piston member, a belt drive means to drive the semi rigid belt and a dose setting mechanism to control the driving of the semi rigid belt is characterised in that the belt drive means comprises a first cable means connected at a first end to a second end of the semi rigid belt and at a second end to a first spool.

Preferably, the dose setting mechanism comprises a dose dial button, a dose setting spindle, a dog to release the dose, a dose setting wheel, a second spool, a second cable means connected between the dose setting wheel and the second spool, and a third spool held against the second cable means between the dose setting wheel and the second wheel by a spring means. More preferably, the dial dose button is connected to the dose setting spindle by a spline.

According to a second aspect of the present invention, an injection device having a housing, is characterised in that the device further comprises a drive mechanism in accordance with the first aspect of the present invention.

Preferably, the housing has an opening in which a retaining pin of the dose dial button may be releasably retained.

Preferably, the housing is provided with a plurality of guide means for the semi rigid belt.

The invention will now be described, by way of example only, with reference to the accompanying drawings in which.

Like reference numerals will be used to refer to like parts of the injection device.

Figure 1:
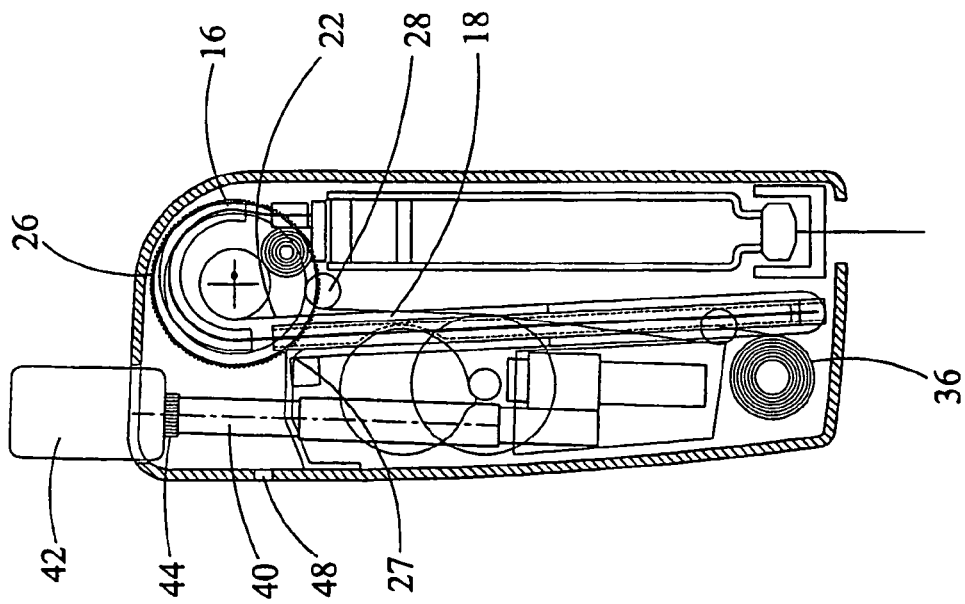
FIG. 1 shows a side section of an injection device having a drive mechanism according to the present invention in which the injection device is closed and a medicament cartridge is full.

Referring first to FIG. 1 there may be seen an injection device in accordance with the present invention. The injection device comprises a main housing 2 and a drive mechanism. A needle unit 4 including a delivery member in the form a hollow needle is secured to a first end of the main housing 2. A medicament cartridge 6 having a first end and a second end may be stored in the main housing 2. When the needle unit 4 is in place, the needle unit 4 pierces a flexible membrane at the first end of the medicament cartridge 6. A displaceable bung 8 is located at the second end of the medicament cartridge 6. A cover (not shown) may be provided over the first end of the main housing 2 to protect the needle unit 4 from damage and a user from inadvertent pricking by the needle. The cover also provides a discrete appearance for the injection device.

The drive mechanism comprises a piston member 10, a semi rigid belt 12 connected to the piston member 10, a belt drive means to drive the semi rigid belt 12 and a dose setting mechanism to control driving of the semi rigid belt 12. The semi rigid belt 12 may be manufactured from any suitable material, for example spring steel or a plastics material. If of plastics material, the piston member 10 and the semi rigid belt 12 may be formed as a unitary component.

The piston member 10 is located adjacent the bung 8 in the medicament cartridge 6. The piston member 10 is connected to a first end of the semi rigid belt 12. Guide means are provided in the main housing to constrain and to direct the semi rigid belt 12. In the illustrated embodiment, first, second and third guide means are shown. The first guide means 14 is located in the region of the first end of the medicament cartridge 6 to direct the piston member 10 towards the bung 8 located within the medicament cartridge 6. The second guide means 16 is substantially U shaped. The third guide means 18 is generally linear in configuration and located to one side of the medicament cartridge 6. A stopper 20 is provided in the third guide means 18. The stopper 20 is free to travel along the third guide means 18.

A first end of the first cable means 22 is connected to a shaft of a first spool 24. The first cable means 22 is adapted to be wound about the first spool on rotation of the first spool 24. The first spool 24 further comprises an inner gear and an outer toothed gear 26. The first cable means 22 extends from the first spool 24 about the stopper 20 and is secured at a second end to a fixed point 27 located within the main housing 2. The first cable means 22 is free to slide over the stopper 20. The first cable means 22, the first-third guide means 14, 16 and 18, and the stopper 20 constitute the belt drive means.

A first roller or pulley 28 is adapted to rotate about a fixed axis and has a peripheral edge. A second cable means 30 is adapted to run between the first roller or pulley 28 and a dose setting wheel 32 by way of a second roller or pulley 34. The second roller or pulley 34 is located in a guide (not shown) having a first stop. The second roller or pulley 34 is biased by spring means towards the first stop. In the illustrated embodiment, it may be seen that the spring means comprises a tensator spring 36. A dose limiter wheel 38 runs from a central shaft of the dose setting wheel 32. The dose setting wheel 32 is driven for rotation by a worm located between the dose setting wheel 32 and a dose setting spindle 40.

The dose setting shaft 40 is provided at an end remote from the worm with a dose dial button 42. The dose dial button 42 is connected to the dose setting spindle 40 by a spline 44. The dose dial button is biased away from the worm. Conveniently, the dose dial button 42 is provided with a retaining pin 46 which engages with an opening 48 in the main housing to retain the dose dial button 42 within the housing 2 as and when required.

A dog 50 in the form of a tine or similar is provided in the housing 2. In a relaxed position, the dog 50 is in contact with the outer toothed gear 26 of the first spool to prevent rotation of the first spool 24. When the dose dial button 42 is retained within the housing 2, the dog 50 is displaced out of contact with the toothed gear 26 of the first spool 24, thereby allowing the first spool 24 to rotate.

In FIG. 1, the injection device is in a closed or "off" position. The dose dial button 42 is retained within the housing 2.

Figure 2:
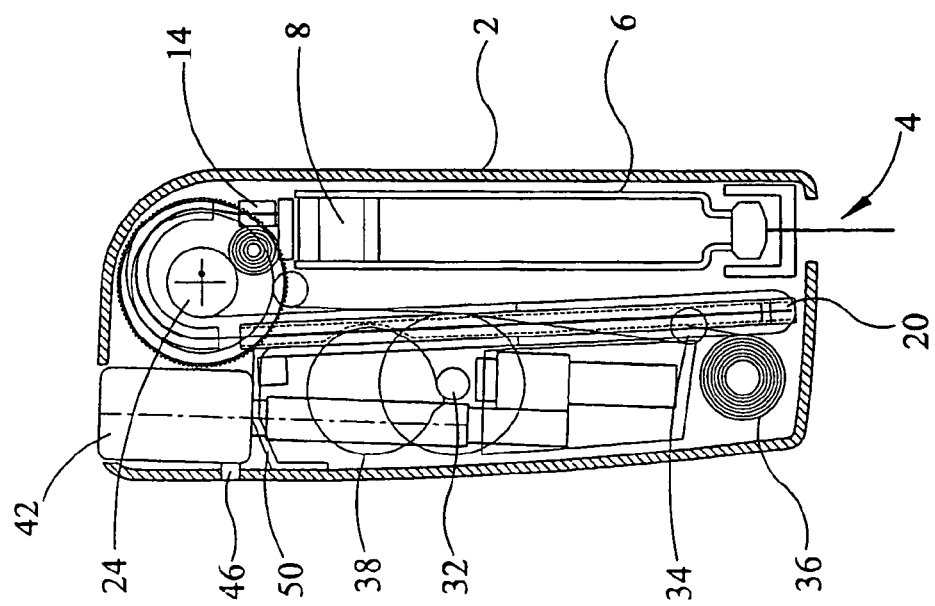
FIG. 2 shows a side section similar to FIG. 1 with the injection device ready for use.

In order to operate the injection device, a user first releases the dose dial button 42, for example by displacing the retaining pin 46 from the opening 48 in the main housing 2. This allows the dog 50 to engage with the toothed gear 26 of the first spool 24 thereby to prevent rotation of the first spool 24 (FIG. 2).

Figure 3:
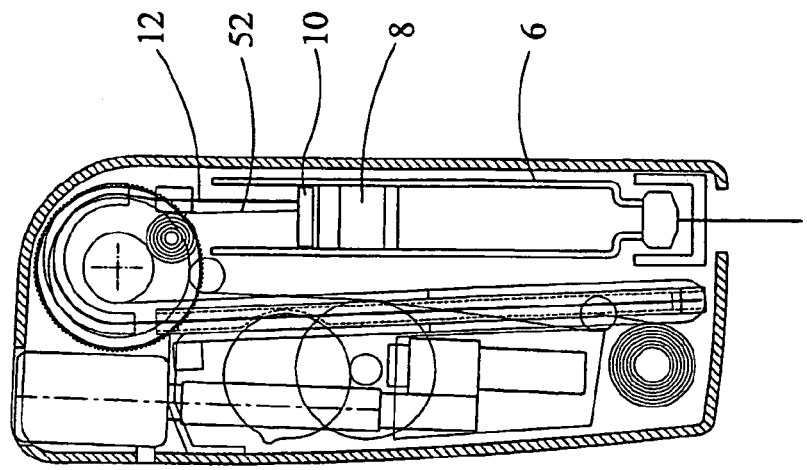
FIG. 3 shows a side section similar to FIG. 1 with a dosage of medicament dialed.
Figure 4:
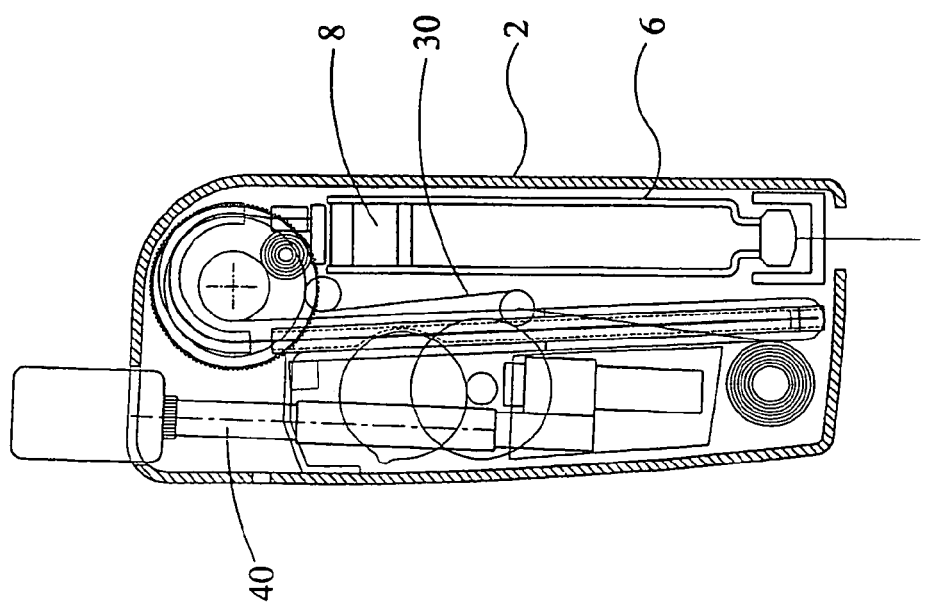
FIG. 4 shows a side section similar to FIG. 1 with the dosage delivered.

The user may now rotate the dose dial button 42. This causes the dosing setting shaft 40 to rotate, and so via the worm, the dose setting wheel 32 rotates a corresponding amount. This has two effects. First, the dose limiter wheel 38 is rotated. This can be used to provide a visual indication to the user of the size of medicament remaining in the medicament cartridge 6. Second, the second cable means 30 is wound onto the dose setting wheel 32, thereby shortening the effective length of the second cable means 30. It is noted that the first roller or pulley 28 is not free to rotate since it is held in position by the first spool which in turn is held by the dog 50. The effective shortening of the second cable means 30 thus draws these controller or pulley 34 along the second roller or pulley guide away from the stop, thereby extending the tensator spring 36 (FIG. 3).

To deliver the dialled dose, the user depresses the dose dial button 42 to retain the dose dial button 42 in the main housing 2. Depressing the dose dial button 42 in this way disengages the dog 50 from the toothed gear 26 of the first spool 24, thereby allowing rotation of the first spool 24 and the first roller or pulley 28. The dose setting wheel 32 is held against rotation by the dose setting spindle 40. Thus, as the tensator spring 36 draws the second roller or pulley 34 back towards the stop, the first roller or pulley 28 is caused to rotate as the second cable means 30 is pulled from the first roller or pulley 28. Rotation of the first roller or pulley 28 then in turn causes the first spool 24 to rotate. Rotation of the first spool 24 causes the first cable means 22 to be drawn onto the first spool 24 thereby drawing the semi rigid belt 12 along the third guide means 18. This, in turn, causes the piston member 10 to be urged towards the bung 8 in the medicament cartridge 6.

This process may be repeated until the medicament cartridge 6 is empty, the medicament cartridge 6 contains insufficient medicament to deliver a dialled dose or some other condition is met. The piston member 10 may then be withdrawn to allow replacement of the medicament cartridge 6. In the illustrated embodiment a second tensator spring 52 is provided for this purpose. If the dog 50 is disengaged from the toothed gear 26 while the dose dial button 42 is outside the housing 2, the components of the injection device will return to the positions shown in FIG. 1.

It can be seen that since the second roller or pulley is urged in a first direction by the tensator spring 36 and concurrently urged in an opposing direction under the action of the second cable means 30, the second roller or pulley guide means maybe omitted. In such a case, the second roller or pulley guide means stop is replaced by an equilibrium position determined by the tensator spring 36 and the second cable means 30 acting on the second roller or pulley 34.

What is claimed is:

1. A drive mechanism for an injection device in which a piston is successively moved in relation to a first end of a medicament cartridge containing a medicament selectively to drive a bung closing the first end of the medicament cartridge into the medicament cartridge to expel medicament through a delivery member located at a second end of the medicament cartridge, the drive mechanism comprising:
   a piston member,
   a semi-rigid belt connected at the first end to the piston member,
   a belt drive means to drive the semi-rigid belt and
   a dose setting mechanism to control the driving of the semi-rigid belt,
wherein the belt drive means comprises a first cable means connected at the first end to a rotatable spool and at the second end to a fixed point on the housing, guide means within which the semi-rigid belt is adapted to be guided, a stopper movably located within the guide means, such that rotation of the spool causes the first cable means to move the stopper within the guide means to drive the semi-rigid belt.

2. A drive mechanism for an injection device according to claim 1, wherein the dose setting mechanism comprises a dose dial button, a dose setting spindle, a dog to release the dose, a dose setting wheel, a first roller or pulley, a second cable means connected between the dose setting wheel and the first roller or pulley, and a second roller or pulley held against the second cable means between the dose setting wheel and the second wheel by a spring means.

3. A drive mechanism for an injection device according to claim 2, wherein the dial dose button is connected to the dose setting spindle by a spline.

4. An injection device having a housing, the injection device comprising a drive mechanism according to claim 2.

5. An injection device according to claim 4, wherein the housing has an opening in which a retaining pin of the dose dial button may be releasably retained.

6. An injection device according to claim 5, wherein the housing is provided with a plurality of guide means for the semi-rigid belt.

7. An injection device according to claim 4, wherein the housing is provided with a plurality of guide means for the semi-rigid belt.

8. An injection device having a housing, injection device comprising a drive mechanism according to claim 1.

* * * * *